US008032212B2

(12) United States Patent
Bornzin et al.

(10) Patent No.: US 8,032,212 B2
(45) Date of Patent: Oct. 4, 2011

(54) SYSTEM AND METHOD FOR MONITORING THORACIC FLUID LEVELS BASED ON IMPEDANCE USING AN IMPLANTABLE MEDICAL DEVICE

(75) Inventors: Gene A. Bornzin, Simi Valley, CA (US); Steve Koh, South Pasadena, CA (US); Euljoon Park, Valencia, CA (US)

(73) Assignee: Pacesetter, Inc., Sylmar, CA (US)

(*) Notice: Subject to any disclaimer, the term of this patent is extended or adjusted under 35 U.S.C. 154(b) by 441 days.

(21) Appl. No.: 12/210,848

(22) Filed: Sep. 15, 2008

(65) Prior Publication Data
US 2010/0069778 A1 Mar. 18, 2010

(51) Int. Cl.
*A61B 5/02* (2006.01)
*A61B 5/08* (2006.01)
*A61B 5/05* (2006.01)
*A61N 1/00* (2006.01)

(52) U.S. Cl. ........ 600/547; 600/484; 600/485; 600/486; 600/506; 600/538; 607/2; 607/18

(58) Field of Classification Search .......... 600/484–486, 600/506, 509, 538, 547; 607/2, 18, 80
See application file for complete search history.

(56) References Cited

U.S. PATENT DOCUMENTS

| 5,174,286 | A | * | 12/1992 | Chirife | 607/11 |
| 6,512,949 | B1 | | 1/2003 | Combs et al. | |
| 6,512,952 | B2 | | 1/2003 | Stahmann et al. | |
| 6,628,988 | B2 | | 9/2003 | Kramer et al. | |
| 6,643,546 | B2 | | 11/2003 | Mathis et al. | |
| 7,308,311 | B2 | * | 12/2007 | Sorensen et al. | 607/32 |
| 7,340,296 | B2 | * | 3/2008 | Stahmann et al. | 600/547 |
| 7,422,560 | B2 | * | 9/2008 | Hatlestsad et al. | 600/300 |
| 7,630,763 | B2 | * | 12/2009 | Kwok et al. | 607/6 |
| 7,676,266 | B1 | * | 3/2010 | Kroll | 607/18 |
| 7,899,522 | B1 | * | 3/2011 | Koh et al. | 600/513 |
| 2003/0120164 | A1 | * | 6/2003 | Nielsen et al. | 600/513 |
| 2004/0102712 | A1 | * | 5/2004 | Belalcazar et al. | 600/547 |
| 2004/0102721 | A1 | | 5/2004 | Belalcazar et al. | |

(Continued)

FOREIGN PATENT DOCUMENTS
EP 1011802 B1 6/2004
(Continued)

OTHER PUBLICATIONS

Extended European Search Report, dated Dec. 1, 2009—EP App. No. 09252059.2.

*Primary Examiner* — Max Hindenburg
*Assistant Examiner* — Sean P Dougherty

(57) ABSTRACT

Techniques are provided for monitoring thoracic fluid levels based on thoracic impedance ($Z_T$) and cardiogenic impedance ($Z_C$). In one example, the implantable device tracks the maximum time rate of change in cardiogenic impedance (i.e. max($dZ_C/dt$)) to detect trends toward hypervolemic or hypovolemic states within the patient based on changes in heart contractility. The detection of these trends in combination with trends in thoracic impedance allows for a determination of whether the thoracic cavity of the patient is generally "too wet" or "too dry," and thus allows for the titration of diuretics to avoid such extremes. In particular, a decrease in thoracic impedance ($Z_T$) in combination with a decrease in max ($dZ_C/dt$) is indicative of the thorax being "too wet" (i.e. a fluid overload). Conversely, an increase in thoracic impedance ($Z_T$) in combination with a decrease in max ($dZ_C/dt$) is indicative of the thorax being "too dry" (i.e. a fluid underload).

18 Claims, 7 Drawing Sheets

U.S. PATENT DOCUMENTS

| | | |
|---|---|---|
| 2004/0220632 A1 | 11/2004 | Burnes |
| 2005/0090753 A1 | 4/2005 | Goor et al. |
| 2005/0109338 A1* | 5/2005 | Stahmann et al. ....... 128/204.18 |
| 2005/0182447 A1* | 8/2005 | Schecter ............................ 607/2 |
| 2005/0216067 A1 | 9/2005 | Min et al. |
| 2006/0184060 A1 | 8/2006 | Belalcazar et al. |
| 2006/0258952 A1 | 11/2006 | Stahmann et al. |
| 2006/0293609 A1 | 12/2006 | Stahmann et al. |
| 2007/0088220 A1 | 4/2007 | Stahmann et al. |
| 2007/0142733 A1* | 6/2007 | Hatlestad et al. ............. 600/508 |
| 2007/0239054 A1* | 10/2007 | Giftakis et al. ............... 600/513 |
| 2008/0091114 A1* | 4/2008 | Min et al. ...................... 600/508 |
| 2008/0125826 A1 | 5/2008 | Belalcazar et al. |
| 2008/0194998 A1* | 8/2008 | Holmstrom et al. .......... 600/595 |
| 2008/0215108 A1* | 9/2008 | Zhu et al. ........................ 607/17 |
| 2008/0243025 A1* | 10/2008 | Holmstrom et al. .......... 600/547 |
| 2008/0262361 A1* | 10/2008 | Gutfinger et al. ............. 600/486 |
| 2008/0300504 A1* | 12/2008 | Lefkov et al. ................. 600/547 |
| 2009/0012416 A1* | 1/2009 | Belalcazar et al. ........... 600/529 |
| 2009/0099475 A1* | 4/2009 | Bjorling ........................ 600/547 |
| 2010/0113961 A1* | 5/2010 | Ohlander et al. ............. 600/547 |

FOREIGN PATENT DOCUMENTS

| | | |
|---|---|---|
| EP | 1582233 A2 | 10/2005 |
| EP | 1582233 A3 | 6/2006 |
| WO | 2004101062 A2 | 11/2004 |
| WO | 2004101062 A3 | 11/2004 |
| WO | 2006068566 A1 | 6/2006 |
| WO | 2007043923 A1 | 4/2007 |
| WO | 2007105996 A1 | 9/2007 |
| WO | 2008103078 A1 | 8/2008 |

* cited by examiner

SYSTEM AND METHOD FOR MONITORING THORACIC FLUID LEVELS BASED ON IMPEDANCE USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for (1) monitoring thoracic fluid levels within patients using such devices, particularly patients with heart failure or pulmonary edema, and for (2) controlling the administration of diuretics to maintain thoracic fluid levels within optimal ranges.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a biventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al. entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

In view of the potential severity of heart failure, it is highly desirable to track the progression of the condition so that appropriate therapy can be provided. Many patients suffering heart failure already have pacemakers or ICDs implanted therein or are candidates for such devices. Accordingly, it is desirable to provide such devices with the capability to automatically track progression of heart failure. Some aspects of the present invention are directed to this end.

Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs, particularly pulmonary venous pressure. The increased pressure pushes fluid—but not blood cells—out of the blood vessels and into lung tissue and air sacs (i.e. the alveoli). This can cause severe respiratory problems and, left untreated, can be fatal. Pulmonary edema can also arise due to other factors besides heart failure, such as infections.

One therapy delivered to address pulmonary edema is to administer diuretics to the patient in an effort to reduce the amount of fluids within the thorax of the patient. One technique uses thoracic electrical impedance measurements to detect a "fluid overload," i.e. a significant increase in thoracic fluids. A drop in thoracic impedance is deemed to be indicative of such a fluid overload. In response, diuretics such as furosemide or bumetanide are administered to the patient to reduce the fluid overload. (Diuretics are drugs that increase the flow of urine, thus eliminating water from the body, ultimately reducing thoracic fluid levels.)

The use of electrical impedance is promising since thoracic impedance can be readily measured in situ using pacemaker or ICDs. However, a significant concern with thoracic impedance-based techniques is that the thoracic impedance measurement provides only a relative measurement of thoracic fluid levels, i.e. the technique merely detects a drop in impedance indicative of a possible increase in thoracic fluid levels. It does not necessarily establish that thoracic fluid levels have increased beyond an acceptable range. Moreover, impedance drops can occur frequently within some patients without any clinical consequences and are often merely "false positive" events. When titrating a patient with diuretics based on such drops in thoracic impedance, it is thus possible to overcorrect the fluid overload by dispensing too much diuretic. The patient may then become hypovolemic (a condition wherein there is too little blood).

Accordingly, it would also be desirable to provide improved techniques for monitoring thoracic fluid levels, which avoid the aforementioned problems, and it is to this end that aspects of the invention are primarily directed. It is particularly desirable to provide techniques for titrating diuretics within patients to keep thoracic fluid levels within an optimal range and such techniques are described herein.

SUMMARY OF THE INVENTION

In accordance with the invention, techniques are provided for monitoring thoracic fluids within a patient having an implantable medical device. In one example, the device detects both thoracic impedance ($Z_T$) and cardiogenic impedance ($Z_C$), i.e. an impedance signal representative of the beating of the heart of the patient. The device then monitors thoracic fluids based on a combination of thoracic impedance and cardiogenic impedance. By exploiting cardiogenic impedance in addition to thoracic impedance, thoracic fluids can be monitored more effectively to, for example, allow for proper titration of diuretics to maintain fluids within an optimal zone for the patient (as specified in advance by the physician or other caregiver.)

In this regard, although thoracic impedance is helpful for determining whether thoracic fluid levels are generally increasing or decreasing, the additional use of cardiogenic impedance permits a more effective determination of whether thoracic fluid levels have deviated from an acceptable or optimal range. In particular, cardiogenic impedance is affected by heart contractility, which is in turn affected by overall blood fluid levels. If the patient becomes either hypervolemic or hypovolemic (i.e. too much or too little fluid in the blood), heart contractility tends to decrease, which, in turn, causes a decrease in the maximum time rate of change in cardiogenic impedance (i.e. max($dZ_C/dt$)).

Accordingly, in at least some embodiments of the invention, max($dZ_C/dt$) is monitored to detect trends toward hypervolemic or hypovolemic states within the patient. The detection of these trends in combination with trends in thoracic impedance levels allows for a determination of whether the thoracic cavity of the patient is generally "too wet" or "too dry," and thus allows for the titration of diuretics to avoid such extremes. For example, a decrease in thoracic impedance ($Z_T$) in combination with a decrease in max ($dZ_C/dt$) is indicative of the thorax being "too wet" (i.e. a fluid overload). Conversely, an increase in thoracic impedance ($Z_T$) in combination with a decrease in max ($dZ_C/dt$) is indicative of the thorax being "too dry" (i.e. a fluid underload).

In an exemplary embodiment, thoracic impedance is detected by the implantable medical device using leads implanted within the heart by delivering impedance detection pulses along a first detection vector between a left ventricular (LV) coil shocking electrode (or an LV pacing electrode) and an electrode mounted to the housing or "can" of the device. Cardiogenic impedance is instead detected using impedance detection pulses delivered along a second detection vector between the LV pacing electrode and a right ventricular (RV) pacing electrode. Alternatively, a single impedance detection vector may be used, with the thoracic and cardiogenic components of the impedance signal identified and extracted using appropriate filters. Max($dZ_C/dt$) is then determined from $Z_C$ for use in combination with $Z_T$ to detect trends toward thoracic fluid overload or underload. In this regard, max($dZ_C/dt$) decreases with diminishing heart contractility (which, as noted, is indicative of trends toward hypervolemic or hypovolemic states.) Hence, max($dZ_C/dt$) may be used in combination with $Z_T$ to detect trends toward thoracic fluid states that are "too wet" or "too dry." Alternatively, rather than using max($dZ_C/dt$), the peak-to-peak excursion within the cardiogenic impedance signal may be exploited. Preferably, when using peak-to-peak excursion, the cardiogenic impedance signal is detected between a right atrial (RA) coil and the device housing.

In one illustrative embodiment, an implantable drug pump containing suitable diuretics is employed. The implantable medical device directly controls the delivery and titration of the diuretics so as to maintain the patient's thoracic fluids within an optimal range. In other embodiments, the implantable device transmits information to an external device (such as a bedside monitor or hand-held interface device) for notifying the patient or caregiver of the need to adjust the dosage of diuretics. For example, if the analysis of cardiogenic and thoracic impedance trends indicates a trend toward fluid overload, the dosage of diuretics is increased (or initiated). If, instead, the analysis indicates the patient is becoming hypovolemic, the dosage of diuretics is decreased or suspended. An expert system may be used, either within the implanted device or within an external system, to determine the proper diuretic dosages for a particular patient so as to maintain fluid levels within an optimal range. In some examples, if adjustments to diuretic dosages do not maintain fluid levels within the optimal range, a physician is notified. Still further, long-term trend information in both cardiogenic and thoracic impedance may be generated and analyzed for tracking the progression or regression of heart failure.

Thus, in at least some embodiments, an impedance-based metric is provided to prevent unnecessary false positive diuresis, excessive diuresis, and to help maintain the patient in an optimal state of fluids—neither "too wet" nor "too dry."

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
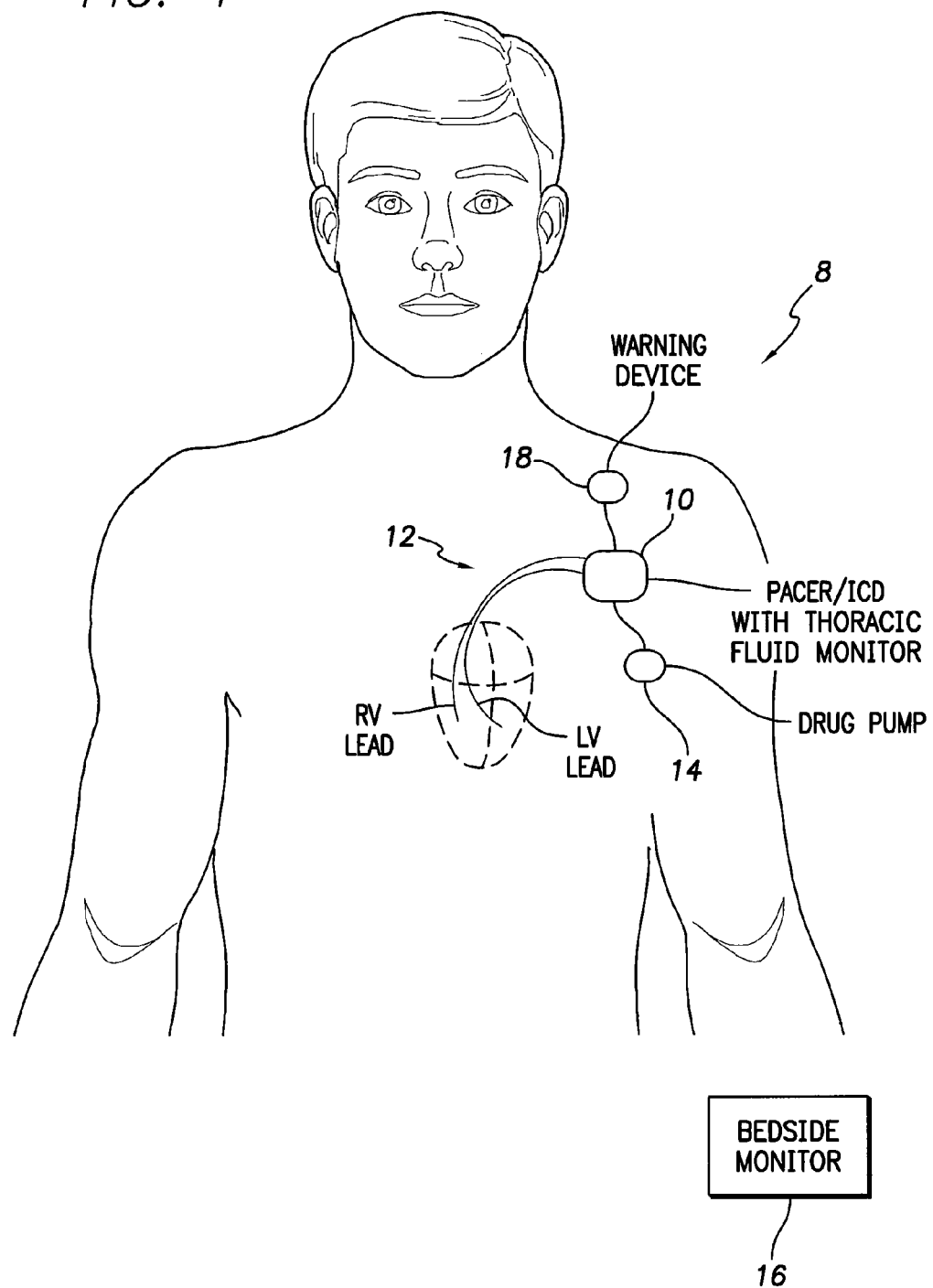
FIG. 1 illustrates pertinent components of an implantable medical system having a pacemaker or ICD capable of monitoring thoracic fluid levels based on thoracic impedance and cardiogenic impedance.

FIG. 1 illustrates an implantable medical system 8 capable of monitoring thoracic fluid levels using both cardiogenic impedance and thoracic impedance. The system is further capable of titrating dosages of diuretics to maintain thoracic fluid levels within optimal or preferred ranges. To these ends, medical system 8 includes a pacer/ICD 10 or other cardiac rhythm management device capable of applying impedance detection pulses to patient thoracic tissues (including heart tissues) via one or more cardiac sensing/pacing leads 12 implanted within the heart of the patient. (In FIG. 1, two exemplary leads are shown—an RV lead and an LV lead, in stylized form. A more complete set of leads is set forth in FIG. 6.)

Thoracic impedance and cardiogenic impedance signals are detected based on the impedance detection pulses, with which the pacer/ICD detects and monitors trends in thoracic fluids. In some embodiments, the pacer/ICD additionally tracks progression of heart failure or pulmonary edema based on long-term trends in thoracic fluids. The pacer/ICD may also be programmed to titrate diuretics to maintain thoracic impedance within a predetermined range. For example, as shown, the implantable system may be equipped with a drug pump 14 capable of the delivering diuretics or other medications to patient tissues in an attempt to maintain thoracic fluids within an optimal range. In other embodiments, information pertaining to thoracic fluid levels is transmitted to an external system, such as bedside monitor 16, which generates diagnostic displays instructing the patient to take certain dosages of or other medications.

In addition, warning signals may be generated using either the bedside monitor 16 or an internal warning device 18 to warn the patient of any significant deviation from the optimal thoracic fluid range, particularly any deviation not compensated for by prior adjustments to diuretic dosages. Internal warning device 18 may be a vibrating device or a "tickle" voltage device that, in either case, provides perceptible stimulation to the patient to alert the patient. The bedside monitor may provide audible or visual alarm signals to alert the patient, as well as any appropriate textual or graphic displays. In addition, diagnostic information pertaining to changes in thoracic fluid levels (and to any medical conditions detected therefrom) may be stored within the pacer/ICD for subsequent transmission to an external programmer (not shown in FIG. 1) for review by a physician during a follow-up session between patient and physician. The physician then prescribes any other appropriate therapies to address the condition. The physician may also adjust the operation of the pacer/ICD to activate, deactivate or otherwise control any therapies that are automatically applied. In addition, the bedside monitor may be directly networked with a centralized computing system for immediately notifying the physician or other caregiver.

Additionally, the pacer/ICD performs a wide variety of pacing and/or defibrillation functions such as delivering pacing is response to an arrhythmia or generating and delivering defibrillation shocks in response to fibrillation.

Hence, FIG. 1 provides an overview of an implantable system capable of monitoring thoracic fluid levels based on both thoracic impedance and cardiogenic impedance and further capable of titrating diuretics or controlling other forms of therapy and for delivering appropriate warnings, if needed. Embodiments may be implemented that do not necessarily perform all of these functions. Rather, embodiments may be implemented that provide, for example, only for tracking thoracic fluid levels and generating diagnostic information for review. In addition, systems provided in accordance with the invention need not include all the components shown in FIG. 1. In many cases, for example, the implantable system will include only the pacer/ICD and its leads. Drug pumps and warning devices are not necessarily implanted. Some implementations may employ an external monitor for generating warning signals but no internal warning device. These are just a few exemplary embodiments. No attempt is made herein to describe all possible combinations of components that may be provided in accordance with the general principles of the invention. Also, note that, although internal signal transmission lines are shown in FIG. 1 for interconnecting the various implanted components, wireless signal transmission may alternatively be employed. In addition, the particular shape, size and locations of the implanted components shown in FIG. 1 are merely illustrative and may not necessarily correspond to actual implant locations. In particular, preferred implant locations for the leads are more precisely illustrated in FIG. 6.

Overview of Impedance-Based Fluid Level Monitoring Technique

Figure 2:
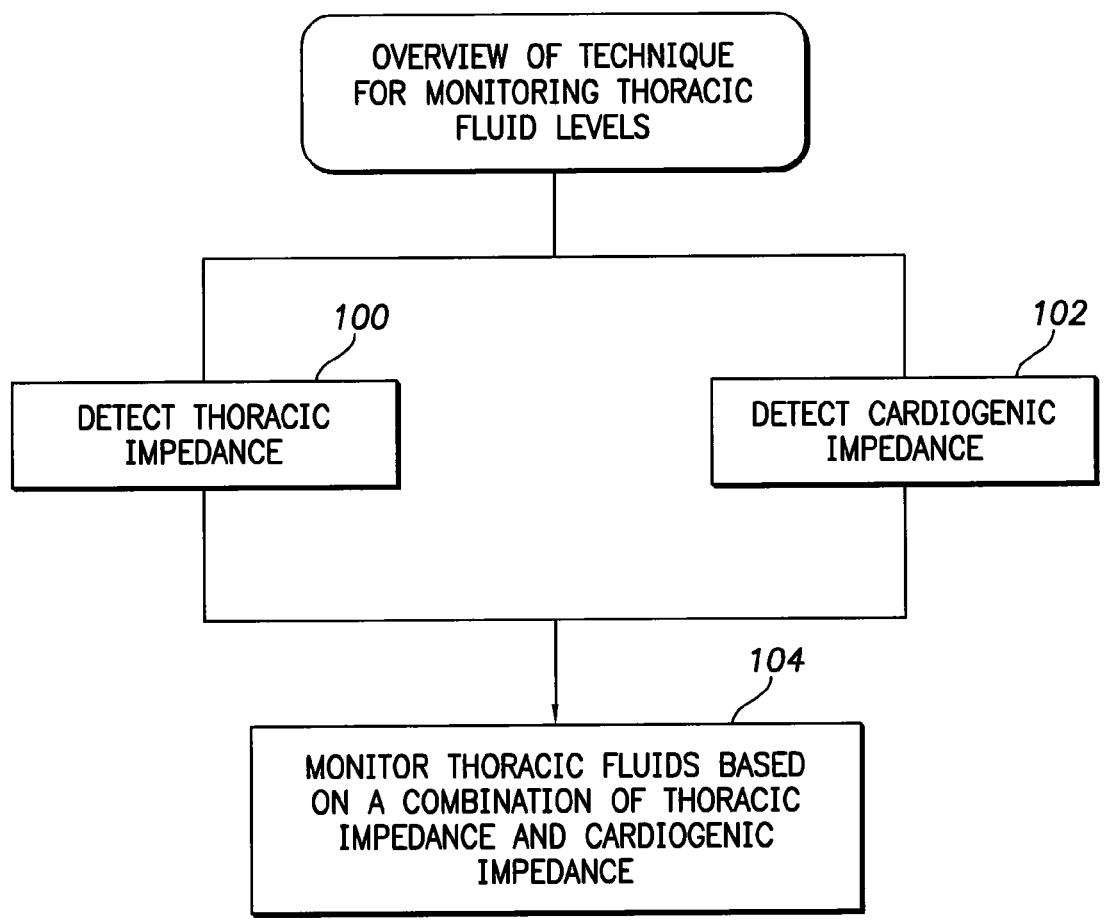
FIG. 2 is a flowchart providing an overview of the impedance-based monitoring technique performed by the system of FIG. 1.

FIG. 2 broadly summarizes the general technique for monitoring thoracic fluids employed by the system of FIG. 1 or other suitably equipped systems. Beginning at steps 100 and 102, the pacer/ICD detects thoracic impedance and cardiogenic impedance, respectively. At step 104, the pacer/ICD then monitors thoracic fluids based on a combination of thoracic impedance and cardiogenic impedance. As noted, thoracic impedance is affected by the degree of thoracic fluids. Cardiogenic impedance is affected by heart contractility. Heart contractility decreases with either excessive or deficient fluid levels. As such, a combination of thoracic impedance and cardiogenic impedance provides an effective "cross-check" tool for assessing thoracic fluid levels.

Figure 3:
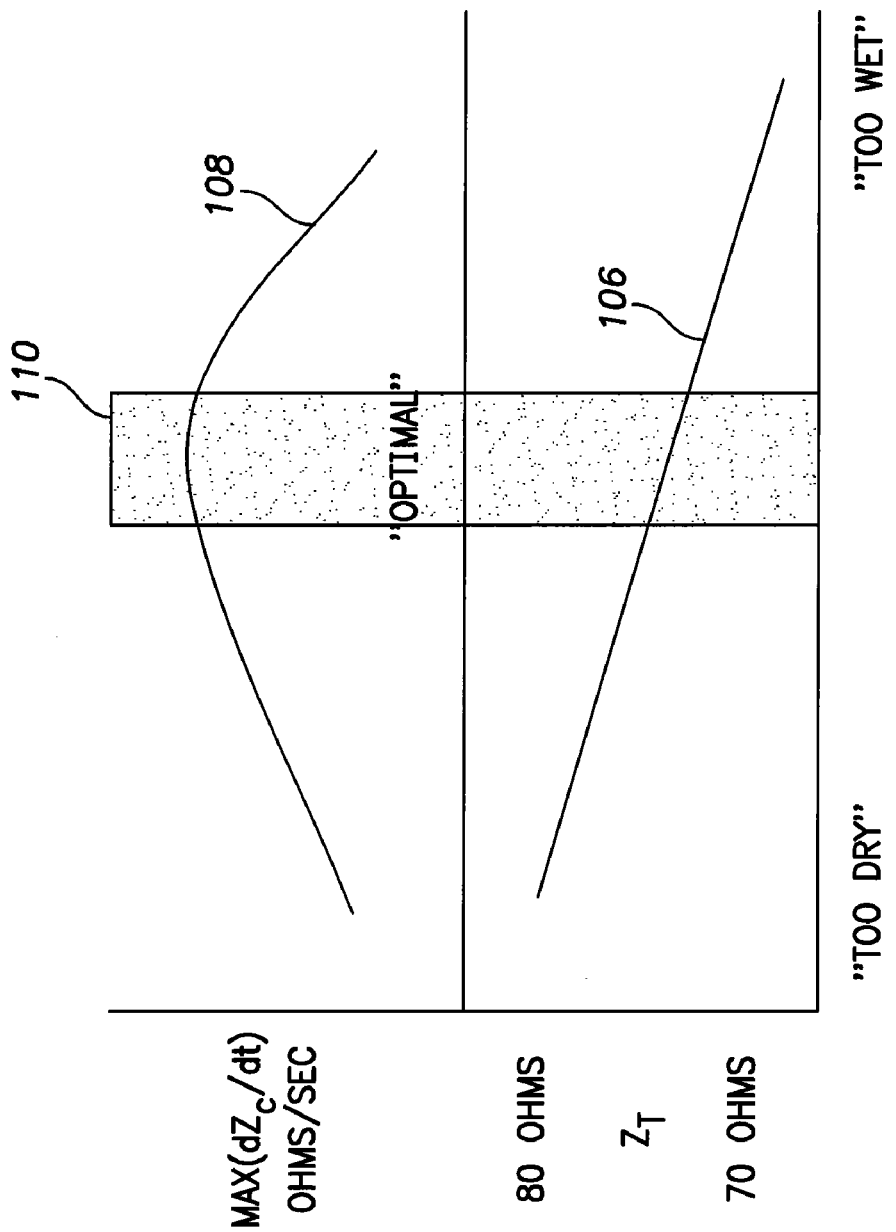
FIG. 3 is a graph illustrating variations in cardiogenic impedance and thoracic impedance relative to thoracic fluid levels, which are exploited by the technique of FIG. 3, and particularly illustrating an optimal thoracic fluid range.

FIG. 3 illustrates the relationship between thoracic impedance $Z_T$ 106 and thoracic fluid levels, which is shown along a scale from "too dry" (i.e. fluid underload) to "too wet" (i.e. fluid overload). Being "too wet" creates a state in which the patient is on the edge of pulmonary edema, while being "too dry" can lead to hypotension. Symptoms of hypotension are decreased blood pressure, and poor peripheral perfusion. The patient may become dizzy and weak. As can be seen, thoracic impedance decreases with increasing thoracic fluid levels.

Additionally, FIG. 3 illustrates the maximum time rate of change in cardiogenic impedance 108 (i.e. $\max(dZ_C/dt)$). As the figure shows, $\max(dZ_C/dt)$ decreases when the thorax is too wet and also when it is too dry. $\text{Max}(dZ_C/dt)$ is at its peak when thoracic fluid levels are within an optimal or preferred range 110. As such, a combination of both thoracic impedance and cardiogenic impedance allows for a robust determination of whether the thoracic fluid levels of the patient are optimal. In particular, whereas a decrease in thoracic impedance merely indicates a relative increase in thoracic fluids, the additional examination of cardiogenic impedance allows for a determination of whether the thoracic fluids are within the optimal range. This allows diuretics to be titrated so as to maintain thoracic fluid levels within the optimal range. This also prevents over-diuresis along with its unnecessary side effects, and improves specificity when dealing with critical situations indicating need for clinical consultation.

Figure 4:
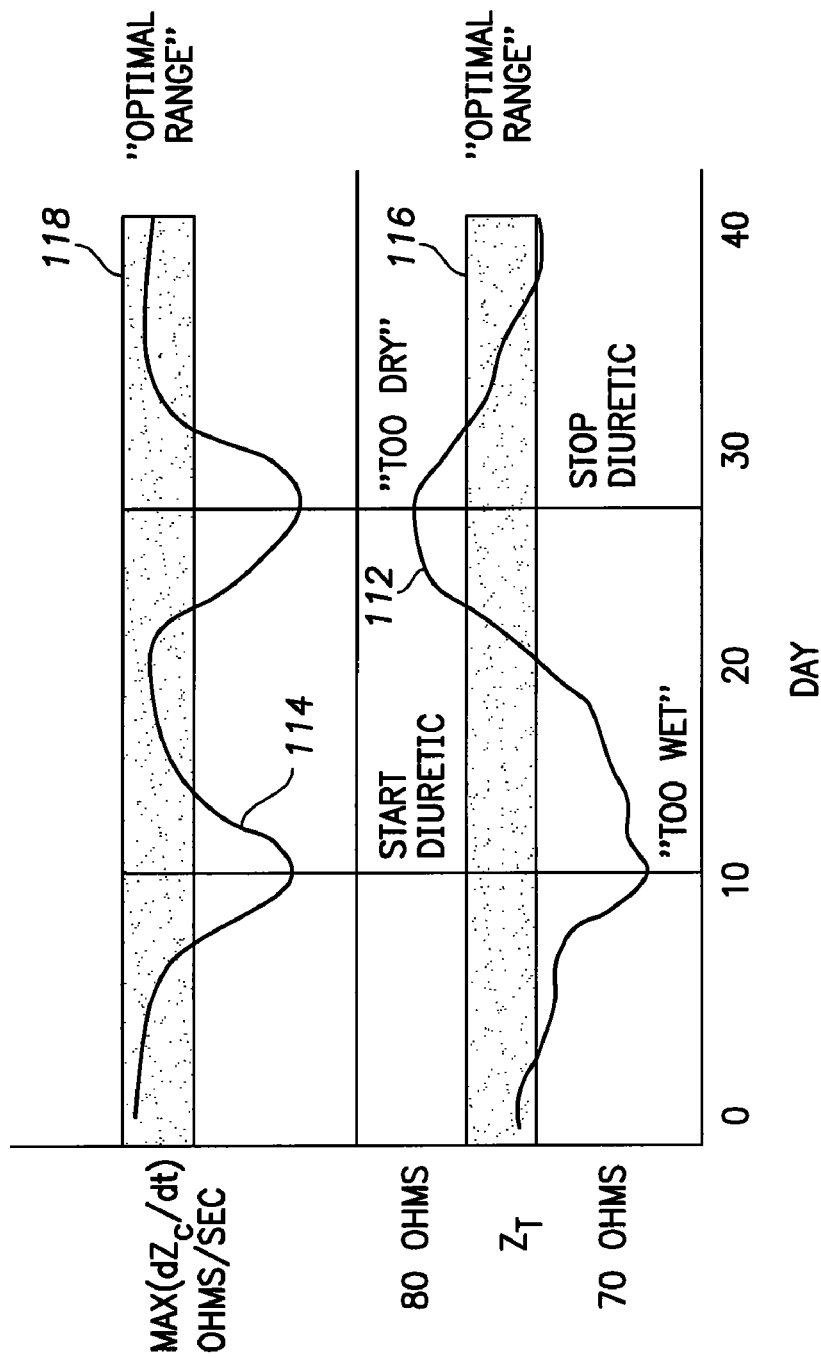
FIG. 4 is a graph illustrating variations or trends in cardiogenic impedance and thoracic impedance values over time exploited by the technique of FIG. 3, and particularly illustrating periods of time wherein impedance values deviate from optimal ranges.

FIG. 4 illustrates changes in thoracic impedance $Z_T$ 112 and cardiogenic impedance (specifically $\max(dZ_C/dt)$) 114 over a period of forty days within a test subject wherein diuretics are titrated in an effort to keep thoracic fluid levels within, or close to, an optimal fluid level range. During a first period of ten days, a fluid overall is building, which is reflected both in changes in thoracic impedance and in cardiogenic impedance. The fluid overload increases fluids within the thoracic cavity, which causes a decrease in thoracic impedance 112. Meanwhile, as the fluid overload builds, the patient tends to become hypervolemic, which decreases heart contractility. It is believed this decrease in heart muscle contractility is due to expansion or stretching of the myocardial muscle caused by the increased blood volume within the chambers of the heart arising due to hypervolemia. The decrease in heart muscle contractility tends to cause a reduction in $\max(dZ_C/dt)$.

In this regard, the cardiogenic impedance signal $Z_C$ represents the beating of the heart of the patient. The slope of $Z_C$ at any given point in time is indicative of the rate at which heart muscle is contracting or expanding at that time. The greater the slope, the faster the contraction or expansion. Hence, the maximum of the time rate of change of $Z_C$ represents the point within each individual heartbeat where the heart muscle is contracting (or expanding) fastest. A decrease in heart muscle contractility (due, e.g., to stretching of the myocardium due to hypervolemia) prevents the heart from beating vigorously and hence $\max(dZ_C/dt)$ values decrease. In use, then, the pacer/ICD monitors cardiogenic impedance and detects the individual $\max(dZ_C/dt)$ value for each heartbeat. The individual values are tracked over time (as shown by trend line 114) to reveal changes, if any, in heart contractility. As explained, the increase in fluids causes a decrease in contractility, which, in turn, causes a decrease in $\max(dZ_C/dt)$ values.

By Day Ten, both the thoracic impedance and the max $(dZ_C/dt)$ values have both dropped below respective optimal ranges 116, 118 indicating a fluid overload, i.e. the patient is "too wet." Diuretics are administered following Day Ten. The diuretics reduce overall blood fluid levels thus also decreasing thoracic fluid levels (and hence causing an increase in thoracic impedance values 112). The reduction in blood fluid levels permits an increase in heart contractility (resulting in a corresponding increase in $\max(dZ_C/dt)$ values 114.) Around Day Twenty, thoracic impedance is again within optimal range 116 and $\max(dZ_C/dt)$ is also within optimal range 118. Continued use of diuretics ultimately results in over-diuresis, i.e. the patient becomes "too dry." As blood fluid levels continue to drop, thoracic impedance increases above its optimal range 116, while $\max(dZ_C/dt)$ again drops below its optimal range 118. The decrease in $\max(dZ_C/dt)$ when the patient becomes "too dry" is again due to a decrease in heart muscle contractility. That is, as blood fluids decrease, the patient becomes hypovolemic, which decreases heart contractility. It is believed this decrease in heart muscle contractility is due to reduced blood volume within the chambers of the heart caused by hypovolemia. In particular, the reduction in blood volume permits the myocardium to contract less vigorously than if the chambers were properly filled, resulting in a reduction in $\max(dZ_C/dt)$).

Around Day 28, when the thoracic impedance and cardiogenic impedance measurements indicate that the patient is "too dry," diuretics are suspended. Thereafter, blood fluid levels again decease, now causing an increase in $\max(dZ_C/dt)$ and a decrease in thoracic impedance, with both values returning to their respective optimal ranges. Eventually, if the impedance values again deviate from their respective optimal ranges, further titration of diuretics may be warranted.

Preferably, diuretics are only titrated if both the thoracic impedance and the $\max(dZ_C/dt)$ values deviate from their optimal ranges. In this regard, $\max(dZ_C/dt)$ might deviate from its optimal range due to changes in heart contractility unrelated to changes in patient fluids (such as changes in heart contractility due to heart disease). As such, an adjustment of diuretic dosages may not be appropriate. Likewise, thoracic impedance might deviate from its optimal range for reasons unrelated to a fluid overload or underload (such as a possible malfunction in thoracic impedance measurements). By using both thoracic impedance and cardiogenic impedance values, unwarranted adjustments diuretics dosages can be avoided.

Thus, FIGS. 2-4 provide a broad overview of a general technique for tracking thoracic fluid levels. A more detailed example will now be presented.

Diuretic Titration Example

Figure 5:
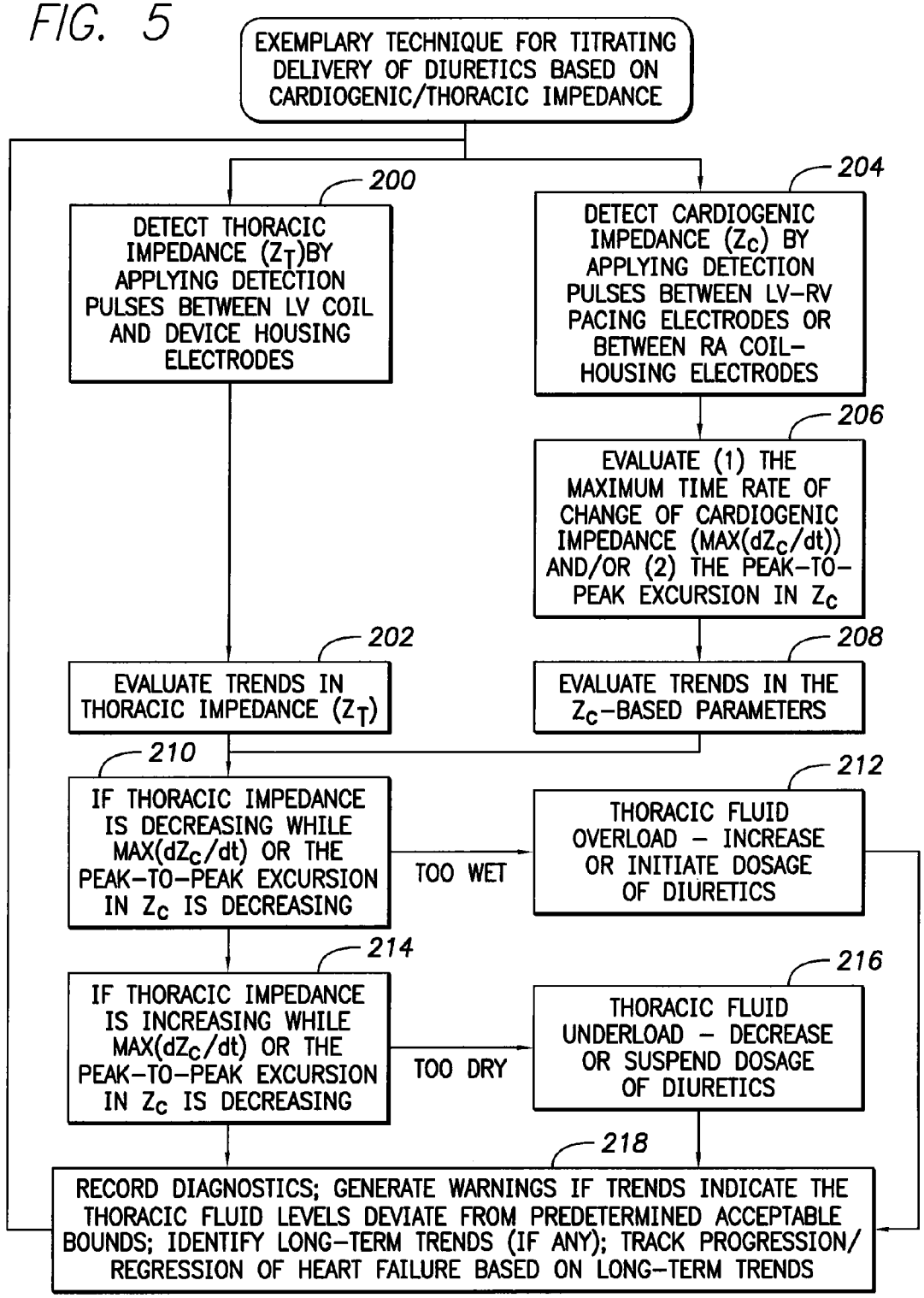
FIG. 5 is a flowchart providing an exemplary technique for maintaining thoracic fluid levels within an optimal range in accordance with the general technique of FIG. 2.

FIG. 5 sets forth an illustrative method for titrating diuretics within a patient based on an examination of thoracic impedance and cardiogenic impedance values. Beginning at step 200, the pacer/ICD detects thoracic impedance ($Z_T$) values by applying detection pulses between the LV shocking coil and an electrode coupled to the device can or housing. A particularly effective tri-phasic impedance detection pulse is described in U.S. patent application Ser. No. 11/558,194 of Panescu et al., filed Nov. 9, 2006, entitled "Closed-Loop Adaptive Adjustment of Pacing Therapy Based on Cardiogenic Impedance Signals Detected by an Implantable Medical Device." However, other suitable impedance detection pulses or waveforms may instead be exploited.

At step 202, the pacer/ICD then evaluates trends (if any) in the thoracic impedance values, such as generally increasing impedance values or generally decreasing impedance values over a period of hours or days. Preferably, the impedance values are digitized and stored in device memory to permit detection of any such trends. Otherwise conventional signal processing techniques may be applied to identify and quantify trends. In a simple example, one or more thresholds are defined to detect deviations from a predetermined optimal thoracic range. Suitable thresholds may be pre-programmed in the pacer/ICD by the manufacturer or specified by the physician during a post-implant follow-up session where the physician programs pacer/ICD parameters. Where appropriate, one or more filters may be applied to the impedance values to isolate or emphasize thoracic impedance. For example, a filter may be used to exclude any higher frequency cardiogenic components of the impedance signal.

Concurrently, beginning at step 204, the pacer/ICD also detects cardiogenic impedance ($Z_C$) by applying similar impedance detection pulses between LV and RV pacing electrodes or between an RA coil and the device housing. Suitable filters may be employed to help isolate the cardiogenic portion of the signal and exclude lower frequency components, such as respiratory components. Alternatively, rather than using one detection vector to detect thoracic impedance and another vector to detect cardiogenic impedance, a single detection vector can be used. To obtain the cardiogenic impedance signal, a low pass filter is applied to filter out respiratory fluctuations and other low frequency fluctuations, leaving only the relatively higher frequency cardiogenic fluctuations. To obtain the thoracic impedance signal, a high pass filter is applied to filter out cardiogenic fluctuations.

At step 206, the pacer/ICD then evaluates (1) the maximum time rate of change of the cardiogenic impedance, i.e. max $(dZ_C/dt)$ and/or (2) the peak-to-peak excursion in $Z_C$. Max $(dZ_C/dt)$ has already been described herein. The peak-to-peak excursion in $Z_C$ instead represents the difference between the maximum and minimum values of the cardiogenic signal within each heartbeat. As with $\max(dZ_C/dt)$, the peak-to-peak excursion in $Z_C$ is affected by changes in contractility arising due to hyper/hypovolemia. In this regard, greater heart muscle contractility generally corresponds to greater peak-to-peak excursions in $Z_C$. $\max(dZ_C/dt)$ is preferably derived from an LV-RV impedance signal; whereas the peak-to-peak excursion in $Z_C$ is preferably derived from an RA coil-housing impedance signal.

At step 208, the pacer/ICD then evaluates trends (if any) in the $Z_C$-based values obtained at 206. As with the thoracic impedance values, the $Z_C$-based values may be digitized and stored in device memory to permit detection of trends. Otherwise conventional signal processing techniques may be applied to identify and quantify any such trends. In some examples, both max($dZ_C/dt$) values and peak-to-peak excursion values are examined to detect trends or deviations from optimal ranges.

At step 210, the pacer/ICD begins titrating diuretics based on the trends (if any) identified at steps 202 and 208. If, at step 210, thoracic impedance is found to be decreasing while max($dZ_C/dt$) or the peak-to-peak excursion in $Z_C$ is found to be decreasing, then a fluid overload (an excess of thoracic fluids) is thereby detected at step 212, i.e. the thorax of the patient is deemed to be "too wet." Diuretics (such as furosemide) are then given to the patient or, if a low dosage is already being given, that dosage is increased, so as to reduce overall patient fluids.

If the pacer/ICD is equipped with an implanted drug pump provided with suitable diuretics, the diuretics may be directly and automatically delivered to the patient. If not, then suitable signals are relayed to a hand-held interface device or transmitted directly to a bedside monitor for instructing the patient or caregiver accordingly. Such instructions might specify the particular diuretic to be taken, as well as its dosage. In some examples, an expert system is provided (either within the pacer/ICD or within the bedside monitor or other external system) for determining the optimal dosage of the diuretic for the patient based, for example, on the history of the patient history, the current dosage levels, the particular trends detected and other information. For example, a rapid change in impedance might warrant a significant change in the dosage of diuretics; whereas a more gradual change in impedance might warrant less significant adjustments in dosage. In addition, such an expert system may be programmed to detect circumstances where prior adjustments to diuretic dosages failed to have the intended effect on patient fluids. The expert system then preferably notifies the physician or caregiver.

If, at step 214, thoracic impedance is instead found to be increasing while max($dZ_C/dt$) or the peak-to-peak excursion in $Z_C$ is decreasing, then a fluid underload (a deficit of thoracic fluids) is thereby detected at step 216, i.e. the thorax of the patient is deemed to be "too dry." Delivery of diuretics is then suspended or, in some cases, the dosage is merely decreased, so as to increase overall patient fluids. Again, the particular response depends, in part, on the capabilities of the implantable system and any external systems used in conjunction therewith. Again, an expert system may be provided to determine the particular response that is appropriate and/or to forward appropriate warning signals to the patient, caregiver or physician.

In one particular example, thoracic impedance for the patient might drop more than five ohms in a week and the cardiogenic impedance might decrease 10%. This triggers the system to deliver or prescribe forty mg of furosemide, at step 212. If the patient improves the next day, then the system returns to a previous dosage level (e.g. a default physician-prescribed dosage for the patient.) However, if the patient does not improve, then furosemide is again prescribed each day. If the thoracic impedance thereafter increases and the cardiogenic impedance shows a decrease in contractility, the titration goal is thereby achieved, and the patient is returned to the basic dosage, at step 216.

In any case, following steps 212 or 216, the pacer/ICD performs step 218 wherein diagnostics are recorded; warning signals are generated (if trends indicate the degree of thoracic fluids deviates from predetermined acceptable bounds or if previous attempts at maintaining optimal fluid levels have not been successful); long-term trends, if any, are identified; and progression/regression of heart failure is tracked. Insofar as the warning signals are concerned, suitable upper and lower impedance-based thresholds can be defined to identify any levels that deviate significantly from acceptable bounds, such that the physician can promptly be warned. In some examples, a short-term three ohm drop in thoracic impedance triggers a warning such that the physician can immediately review the patient's impedance trends. Also, in some examples, if the patient does not show improvement after two days, warnings are also generated.

Note that step 218 is also performed even if no fluid overload or underload is detected. This ensures periodic recordation of suitable diagnostics and periodic examination of long-term trends (i.e. trends occurring over time frames of days to weeks or months.) Such long-term trends might be indicative of progression or regression of heart failure and suitable warning signals can be generated. Note that very short trends might be filtered out by the aforementioned low-pass filters. Preferably, then, absolute values of the impedance parameters are stored within the device for long-term trend detection.

Note also that additional information besides cardiogenic impedance and thoracic impedance may also be exploited, particularly in conjunction with an expert system capable of examining trends in several physiological parameters and drawing conclusions therefrom. For example, the RA coil—housing impedance signal mentioned above is affected by the expansion of the great vessels of the upper chest including the aorta, the aortic arch, the subclavian, and carotid arteries. The expansion of these great vessels relates to cardiac output and blood pressure changes, which are in turn affected by blood fluid levels. The peak-to-peak excursion in the upper thorax impedance signal is related to ejection fraction, which can be separately tracked by the expert system. In other examples, stroke volume might be detected via suitable sensors for use by the expert system. Stroke volume can also be estimated based on LV-RV impedance signal variations. These and other physiological parameters can be analyzed by the expert system along with the aforementioned thoracic and cardiogenic impedance signals to provide a more robust analysis technique.

Still further, note that an examination of long-term changes in blood pressure (derived, e.g., from an examination of the upper thoracic impedance signal or from suitable blood pressure sensors) can also aid in the detection of progression/regression of heart failure by the expert system. In this regard, although congestive heart failure is initially associated with elevated blood pressure, when heart failure progresses to more severe levels the systemic blood pressure drops because the heart does not pump effectively enough to sustain elevated blood pressure.

As can be appreciated, a wide variety of physiological parameters detected by the implantable system can be employed in conjunction with thoracic and cardiogenic impedance to detect and track various conditions and to control therapy.

In the following section, an exemplary pacer/ICD will be described, which includes components for performing the impedance-based detection and evaluation techniques or FIGS. 2-5.

Exemplary Pacer/ICD

Figure 6:
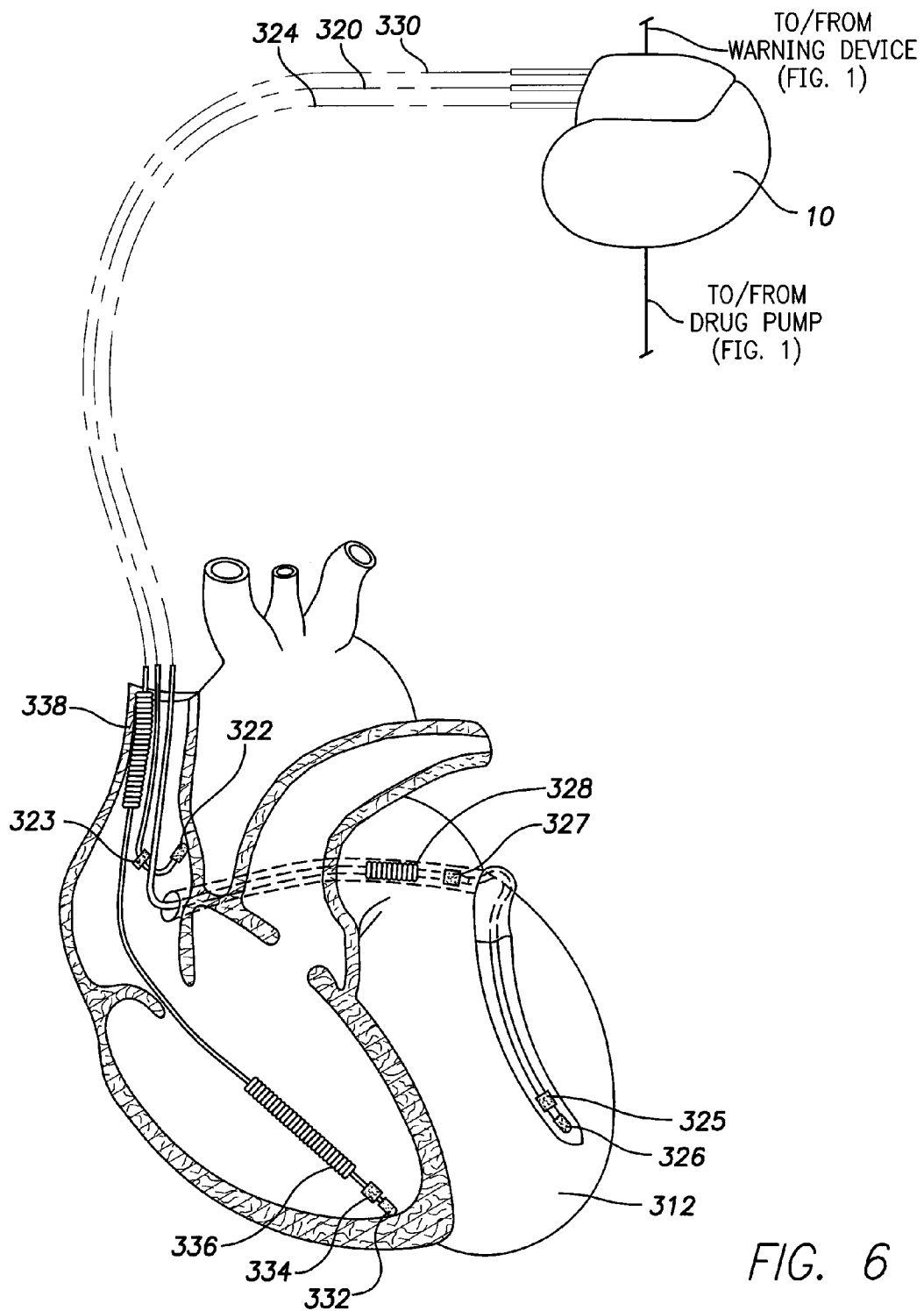
FIG. 6 is a simplified, partly cutaway view, illustrating the pacer/ICD of FIG. 1 along with at set of leads implanted into the heart of the patient.

FIG. 6 provides a simplified block diagram of the pacer/ICD, which is a dual-chamber stimulation device capable of treating both fast and slow arrhythmias with stimulation therapy, including cardioversion, defibrillation, and pacing stimulation, as well as capable of performing the impedance-based functions described above. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 7:
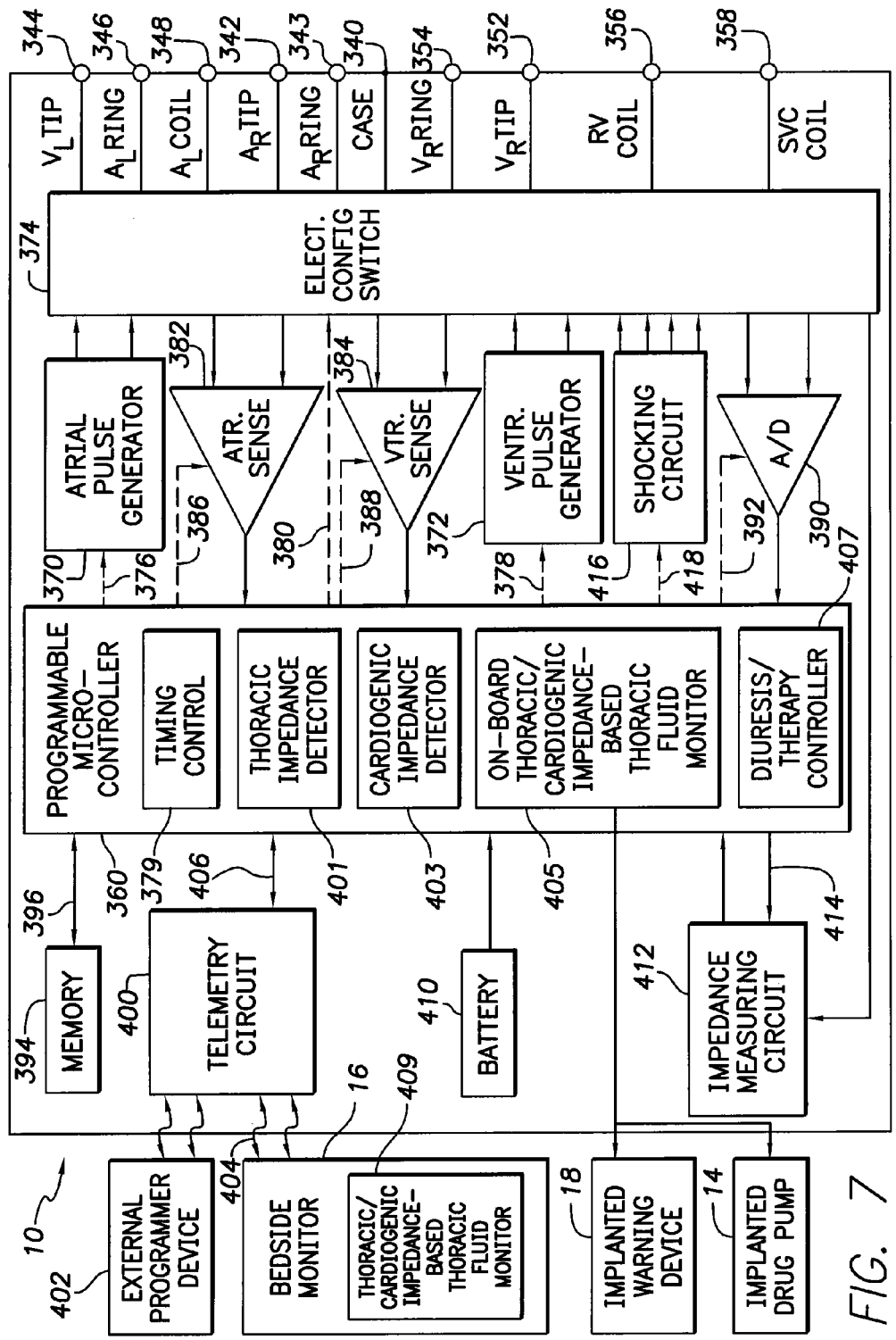
FIG. 7 is a functional block diagram of the pacer/ICD of FIG. 6, illustrating basic circuit elements that provide cardioversion, defibrillation and/or pacing stimulation in the heart and particularly illustrating components for monitoring thoracic fluids using the techniques of FIGS. 2-5.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned impedance-based functions.

The housing 340 for pacer/ICD 10, shown schematically in FIG. 7, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 7, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity.

Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 7. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 7, pacer/ICD 10 is shown as having an impedance measuring circuit 412 which is enabled by the microcontroller 360 via a control signal 414. Herein, impedance is primarily detected for use in evaluating thoracic and cardiogenic impedance for use in evaluating thoracic fluids. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to monitoring thoracic fluids and controlling delivery/prescription of diuretics. More specifically, for the purposes of detecting changes in thoracic fluid levels, the microcontroller includes a thoracic impedance detector 401 and a cardiogenic impedance detector 403. Also provided is an on-board thoracic/cardiogenic impedance-based thoracic fluid monitor 405 operative to monitor thoracic fluids based on a combination of thoracic impedance and cardiogenic impedance. Additionally, or alternatively, an external thoracic/cardiogenic impedance-based thoracic fluid monitor 409 may be provided within bedside monitor 16 or within other external devices.

In either case, the thoracic fluid monitor controls generation of diagnostic data and warning signals based on thoracic and cardiogenic impedance. For on-board implementations, the diagnostic data is stored within memory 394. Warning signals may be relayed to the patient via implanted warning device 18 or via bedside monitor 16. For on-board implementations, the microcontroller also includes a diuresis/therapy controller 407, which controls and titrates the delivery of diuretics (or other appropriate therapies) using the techniques described above. In implementations where there is no on-board thoracic fluid monitor, titration of diuretics is typically achieved by instead providing suitable instructions to the patient or caregiver via the bedside monitor (or other external device).

Depending upon the implementation, the various components of the on-board microcontroller may be implemented as separate software modules or the modules may be combined to permit a single module to perform multiple functions. In addition, although shown as being components of the microcontroller, some or all of these components may be implemented separately from the microcontroller. Both the thoracic fluid monitor and the diuresis controller can exploit or comprise expert systems.

What have been described are various systems and methods for use with a pacer/ICD. However, principles of the invention may be exploiting using other implantable medical systems. Thus, while the invention has been described with reference to particular exemplary embodiments, modifications can be made thereto without departing from the spirit and scope of the invention.

What is claimed is:

1. A method for monitoring thoracic fluids within a patient having an implantable medical device, the method comprising:
   detecting thoracic impedance;
   detecting cardiogenic impedance;
   monitoring thoracic fluids based on a combination of thoracic impedance and cardiogenic impedance;
   wherein monitoring thoracic fluids based on a combination of thoracic impedance and cardiogenic impedance includes detecting trends within thoracic impedance and detecting trends within time rate of change values derived from cardiogenic impedance;
   wherein a decrease in thoracic impedance combined with a decrease in the time rate of change of cardiogenic impedance is deemed to be indicative of excess fluids within the thorax.

2. The method of claim 1 further including controlling therapy in response to changes in thoracic fluid levels.

3. The method of claim 2 wherein controlling therapy in response to changes in thoracic fluid levels includes one or more of initiating or increasing a dosage of diuretics in response to an excess of thoracic fluids.

4. The method of claim 2 wherein controlling therapy in response to changes in thoracic fluid levels includes one or more of suspending or decreasing a dosage of diuretics in response to a deficit of thoracic fluids.

5. The method of claim 2 wherein controlling therapy in response to changes in thoracic fluids includes controlling dosages of diuretics to maintain a thoracic fluid levels within a predetermined range.

6. The method of claim 2 wherein controlling therapy in response to changes in thoracic fluids is controlled by an expert system.

7. The method of claim 1 further including generating diagnostic information representative of changes in thoracic fluid levels.

8. The method of claim 1 further including generating warning signals indicative of thoracic fluid levels deviating from a predetermined range.

9. The method of claim 1 further including generating warning signals indicative of failure of prior therapy to maintain thoracic fluid levels within a predetermined range.

10. The method of claim 1 further including identify long-term trends within thoracic impedance and within cardiogenic impedance indicative of progression of heart failure.

11. The method of claim 1 wherein monitoring thoracic fluids based on a combination of thoracic impedance and cardiogenic impedance is performed by the implantable device.

12. The method of claim 1 wherein monitoring thoracic fluids based on a combination of thoracic impedance and cardiogenic impedance is performed by an external system based information transmitted from the implantable medical device.

13. The method of claim 1 wherein detecting thoracic impedance includes applying impedance detection pulses between one or more of a left ventricular (LV) coil shocking electrode or a LV pacing electrode and an electrode mounted to a housing of the implantable medical device.

14. The method of claim 1 wherein detecting cardiogenic impedance includes applying impedance detection pulses between at least two electrodes to obtain an impedance signal.

15. The method of claim 1 wherein detecting cardiogenic impedance includes applying impedance detection pulses between a right atrial (RA) electrode and an electrode mounted to a housing of the implantable medical device to obtain an RA-housing impedance signal.

16. A method for monitoring thoracic fluids within a patient having an implantable medical device, the method comprising:
   detecting thoracic impedance;
   detecting cardiogenic impedance;
   monitoring thoracic fluids based on a combination of thoracic impedance and cardiogenic impedance;
   wherein monitoring thoracic fluids based on a combination of thoracic impedance and cardiogenic impedance includes detecting trends within thoracic impedance and detecting trends within time rate of change values derived from cardiogenic impedance;

wherein an increase in thoracic impedance combined with a decrease in the time rate of change of cardiogenic impedance is deemed to be indicative of a deficit of fluids within the thorax.

17. A system for monitoring thoracic fluids within a patient having an implantable medical device implanted therein, the system comprising:

a thoracic impedance detector;

a cardiogenic impedance detector;

a thoracic fluid monitor that monitors thoracic fluids based on a combination of thoracic impedance and cardiogenic impedance;

wherein the thoracic fluid monitor monitors thoracic fluids based on a combination of thoracic impedance and cardiogenic impedance including detecting trends within thoracic impedance and detecting trends within time rate of change values derived from cardiogenic impedance;

wherein a decrease in thoracic impedance combined with a decrease in the time rate of change of cardiogenic impedance is deemed to be indicative of excess fluids within the thorax.

18. A system for monitoring thoracic fluids within a patient having an implantable medical device implanted therein, the system comprising:

a thoracic impedance detector;

a cardiogenic impedance detector;

a thoracic fluid monitor that monitors thoracic fluids based on a combination of thoracic impedance and cardiogenic impedance;

wherein the thoracic fluid monitor monitors thoracic fluids based on a combination of thoracic impedance and cardiogenic impedance including detecting trends within thoracic impedance and detecting trends within time rate of change values derived from cardiogenic impedance;

wherein an increase in thoracic impedance combined with a decrease in the time rate of change of cardiogenic impedance is deemed to be indicative of a deficit of fluids within the thorax.

* * * * *